United States Patent [19]

Wright

[11] 4,282,350
[45] Aug. 4, 1981

[54] SELECTIVE 3''-N-ACYLATION OF 1,3''-DI-N-UNPROTECTED-POLY-N-PROTECTED-4,6-DI-O-(AMINOGLYCOSYL)-1,3-DIAMINOCYCLITOLS

[75] Inventor: John J. Wright, Cedar Grove, N.J.

[73] Assignee: Schering Corporation, Kenilworth, N.J.

[21] Appl. No.: 822,118

[22] Filed: Aug. 5, 1977

[51] Int. Cl.³ .............................................. C07H 15/22
[52] U.S. Cl. ..................................... 536/10; 424/180; 536/17 R
[58] Field of Search ......................... 536/10, 17, 17 R

[56] References Cited

U.S. PATENT DOCUMENTS

| 4,044,123 | 8/1977 | Daniels et al. | 536/17 |
| 4,063,015 | 12/1977 | Mallams | 536/17 |
| 4,065,615 | 12/1977 | Horii et al. | 536/17 |
| 4,066,752 | 1/1978 | Mallams et al. | 536/10 |

Primary Examiner—Johnnie R. Brown
Attorney, Agent, or Firm—Mary S. King; Elizabeth A. Bellamy

[57] ABSTRACT

This invention describes a novel process whereby 1,3''-di-N-unprotected-poly-N-protected-4,6-di-O-(aminoglycosyl)-1,3-diaminocyclitols are selectively acylated at the 3''-N-position with 1-Z-imidazole, wherein Z is an amino protecting group; to produce novel 1-N-unprotected-poly-N-protected-4,6-di-O-(aminoglycosyl)-1,3-diaminocyclitols.

10 Claims, No Drawings

SELECTIVE 3″-N-ACYLATION OF 1,3″-DI-N-UNPROTECTED-POLY-N-PROTECTED-4,6-DI-O-(AMINOGLYCOSYL)-1,3-DIAMINOCYCLITOLS

FIELD OF THE INVENTION

This invention relates to a novel process and to novel compositions-of-matter produced thereby. Specifically, this invention relates to a process whereby 1,3″-di-N-unprotected-poly-N-protected-4,6-di-O-(aminoglycosyl)-1,3-diaminocyclitols are selectively protected at the 3″-amino function.

Particularly, this invention relates to a process for preparing 1-N-unprotected-poly-N-acylated derivatives of 4,6-di-O-(aminoglycosyl)-1,3-diaminocyclitol antibiotics including certain gentamicins, sisomicin, verdamicin, tobramycin, Antibiotics G-52, G-418, 66-40B, 66-40D, JI-20A, JI-20B, kanamycin A, kanamycin B, 3′,4′-dideoxykanamycin B and the 5-epi, 5-deoxy, 5-epi-fluoro-5-deoxy derivatives of the foregoing.

Still further, this invention relates to novel 1-N-unprotected-poly-N-protected-4,6-di-O-(aminoglycosyl)-1,3-diaminocyclitols useful as intermediates in the preparation of 1-N-substituted-4,6-di-O-(aminoglycosyl)-1,3-diaminocyclitol antibacterial agents.

PRIOR ART

U.S. Pat. No. 4,002,742, issued Jan. 11, 1977 to Wright, et al., of common assignee, describes a multistep method whereby 4,6-di-O-(aminoglycosyl)-1,3-diaminocyclitols are converted to certain 1-N-unprotected-poly-N-protected-4,6-di-O-(aminoglycosyl)-1,3-diaminocyclitols which are disclosed as intermediates in the preparation of 1-N-alkylated derivatives useful as antibacterial agents, more particularly, 1-N-ethylsisomicin.

French Pat. No. 74-23811 describes the per-N-formylation of an aminoglycoside which is further reacted to produce a 1-N-unprotected-poly-N-formylated aminoglycoside which can be further reacted to produce a 1-N-substituted aminoglycoside.

By my invention, I have developed a novel chemical process whereby a 4,6-di-O-(aminoglycosyl)-1,3-diaminocyclitol, also known herein as an aminoglycoside, is converted to a 1-N-unprotected-poly-N-protected aminoglycoside, many of which were heretofore unknown and could not be prepared by prior art processes. The latter compounds can be further converted to 1-N-substituted aminoglycosides.

A preferred compound of my invention is the heretofore unknown 3,2′,6′,3″-tetra-N-acetylsisomicin which is converted to the known antibacterial 1-N-ethylsisomicin, otherwise known as netilmicin.

GENERAL DESCRIPTION OF THE INVENTION PROCESS ASPECT

The process aspect of this invention resides in the concept of the selective protection of a 3″ amino function in a 1,3″-di-N-unprotected-poly-N-protected-4,6-di-O-(aminoglycosyl)-1,3-diaminocyclitol, wherein the 6-O-aminoglycosyl has an amino function at the 3″ position and hydroxyl functions at the 2″ and 4″ positions, which comprises the reaction of said 1,3″-di-N-unprotected-poly-N-protected-4,6-di-O-(aminoglycosyl)-1,3-diaminocyclitol in a solvent with no greater than one molar equivalent of available 1-Z-imidazole, wherein Z is an amino protecting group selected from lower alkanoyl, lower alkoxycarbonyl, aralkoxycarbonyl, trichloroethoxycarbonyl and N-carbonylimidazole. Thereby is produced 1-N-unprotected-poly-N-protected-4,6-di-O-(aminoglycosyl)-1,3-diaminocyclitols, said compounds being useful as intermediates in the preparation of 1-N-substituted aminoglycosides.

As used in this application, the term "aminoglycoside" refers to a 4,6-di-O-(aminoglycosyl)-1,3-diaminocyclitol, "per-N-protection" refers to protection on all the amino functions of an aminoglycoside, and "poly-N-protection" refers to protection on all amino functions unless otherwise excluded as, for instance, the terminology 1,3″-di-N-unprotected-poly-N-protected.

In an effort to find another process for the production of 1-N-substituted aminoglycosides, especially 1-N-ethylsisomicin I have found a novel process for the selective 3″ amino protection of 1,3″-di-N-unprotected-poly-N-protected aminoglycosides to produce 1-N-unprotected-poly-N-protected aminoglycosides whereby side products/reactions are minimized in the preparation of said 1-N-substituted aminoglycosides.

Chemical transformation on an aminoglycoside wherein the site of reaction is to be one of the amino functions should ideally be carried out on intermediates wherein every other amino function is selectively protected by a blocking group; otherwise, mixtures of various mono-N and poly-N-derivatives are formed which require tedious separation techniques (usually one to several column chromatographies) to isolate the desired transformation product. However, by the prior art methods, it is not always possible to prepare the ideal selectively blocked intermediate, so that with any of the amino functions unprotected, multiple products are produced, and the desired transformation product is therefore obtained in low yields.

In view of the above, it should be obvious that in order to produce a 1-N-substituted aminoglycoside, it will be easier to minimize side reactions and thereby increase yields if one can start with a 1-N-unprotected-poly-N-protected aminoglycoside as intermediate.

In U.S. Pat. No. 4,002,742, which relates to the production of 1-N-substituted aminoglycosides, there is described a multistep method for preparing a 1-N-unprotected-poly-N-protected aminoglycoside, the sequence of steps being as follows: Sisomicin is converted to:

(a) Penta-N-carbobenzyloxysisomicin→
(b) 1,3′,2′,6′-tetra-N-carbobenzyloxy-3″-N-4″-O-carbonylsisomicin→
(c) 3″-N-4″-O-carbonylsisomicin→
(d) 2′,3′,6′-tri-N-t-butoxycarbonyl-3″-N-4″-O-carbonylsisomicin.

The aforementioned process produces the product in inherently low yields. Furthermore, this process cannot produce the N-alkanoyl protected compounds claimed in this invention.

The French Pat. No. 74-23811 describes a method whereby, for example, kanamycin B is formylated to 1,3,2′,6′,3″-penta-N-formylated kanamycin B, thence treated with base to produce 3,2′,6′,3″-tetra-N-formylated kanamycin B. The aforementioned process is, however, restricted to the preparation of formyl derivatives, and is such that the product is produced in low yields (15–25%).

In view of the heretofore inherent problems in blocking all the amino groups, regardless of configuration, other than the 1-N-position in an aminoglycoside, it has been the practice to block some of the amino functions (keeping 1 unblocked), then introduce the 1-N-substituent. Of course, inherent in this is the possibility of getting a multiplicity of compounds wherein substitution has taken place at every unblocked amino function.

Although this invention is more generic in its ultimate application, the presently available and commercially useful compounds in which this invention may be used are gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, Antibiotic G-52, Antibiotic 66-40B, Antibiotic 66-40D, Antibiotic G-418, Antibiotic JI-20A, Antibiotic JI-20B, kanamycin A, kanamycin B, 3',4'-dideoxykanamycin B, verdamicin, sisomicin, tobramycin and the 5-epi, 5-deoxy, 5-epi-fluoro-5-deoxy analogs of the foregoing.

The process of this invention utilizes as starting compounds any one of the aforementioned compounds after the amino groups other than those at the 1 and 3''-positions, have been protected. These 1,3''-di-N-unprotected-poly-N-protected aminoglycosides are prepared using a transition-metal (e.g. copper) complexing process, said process being the subject of U.S. Application Ser. No. 697,297, filed June 17, 1976, now U.S. Pat. No. 4,136,254, of common assignee, hereinafter detailed in the Preparations section and incorporated herein by reference. The protecting groups used here can be lower alkanoyl (acetyl, propionyl, trifluoroacetyl and the like), aroyl (benzoyl), lower alkoxy carbonyl (trichloroethoxycarbonyl, ethoxycarbonyl, t-butoxycarbonyl) and the aralkoxycarbonyl (benzyloxycarbonyl) acetyl being the preferred protecting group. To prepare these requisite starting compounds, for example, a 4,6-di-O-(aminoglycosyl)-1,3-diaminocyclitol containing a 3''-amino-2'',4''-di-hydroxyl group (e.g. sisomicin) is reacted with cupric acetate hydrate, to produce a cupric salt complex which is then reacted with acetic anhydride in an inert organic solvent. Hydrogen sulfide gas is then bubbled through the solution to remove the cupric salt complex and, after chromatography, a 1,3''-di-N-unprotected-poly-N-protected-4,6-di-O-(aminoglycosyl)-1,3-diaminocyclitol (e.g. 3,2',6'-tri-N-acetyl sisomicin) is produced in good yields.

Heretofore, if the aforementioned 1,3''-di-N-unprotected-poly-N-protected-aminoglycoside were further acylated by the prior art methods, it would be expected that the 1-amino function would be preferentially acylated, not the 3''-amino function since the 1 amino function is primary and less hindered than the 3''-amino function, the latter having neighboring 2'' and 4''-hydroxyl functions, and in the case of aminoglycosides such as sisomicin and gentamicin, being a secondary amine. Indeed this is illustrated in Example 3 wherein 1,3''-di-N-unprotected-3,2',6'-tri-N-(trichloroethoxycarbonyl) sisomicin is reacted with N-acetoxysuccinimide, deblocked at the 3,2',6'-amino functions to produce 1-N-acetyl sisomicin (in good yields).

By my invention I have found that in a 1,3''-di-N-unprotected-poly-N-protected aminoglycoside, I can preferentially protect the 3''-N-position by means of 1-Z-imidazole, this reaction taking place cleanly and in good yields. The 1-Z-imidazole is a compound wherein Z is an amino protecting group which is lower alkanoyl (acetyl, propionyl, butyryl, trifluoroacetyl), lower alkoxycarbonyl (ethoxycarbonyl, t-butoxycarbonyl, trichloroethoxycarbonyl), aralkoxycarbonyl (benzyloxycarbonyl) and N-carbonylimidazole. In this invention, 1-Z-imidazole is preferentially 1-lower alkanoylimidazole, 1-acetylimiidazole being the most preferred.

The 1-Z imidazoles are a known class of compounds. Those which are not readily available are conveniently prepared by reaction of imidazole with the appropriate acyl chloride or chloroformate.

By my process the 1,3''-di-N-unprotected-poly-N-protected aminoglycoside is allowed to react with a 1-Z-imidazole in an inert organic solvent, water and/or lower alkanol at ambient temperatures for a period of from about 0.5-24 hours. Using separation techniques described hereinafter in the Examples section, the 1-N-unprotected-poly-N-protected aminoglycoside is obtained. For example, 3,2',6'-tri-N-acetylsisomicin is reacted with acetylimidazole in a water/tetrahydrofuran mixture at room temperature for about 2 hours, then isolated utilizing known techniques to obtain 3,2',6',3''-tetra-N-acetylsisomicin.

The inert organic solvents employed in this process are those which are water miscible but which will not take part in the reaction, e.g. tetrahydrofuran, dioxane, dimethoxyethane, dimethylformamide and acetonitrile. In the instances where inert organic solvents are utilized alone, the ratio of the imidazole to the aminoglycoside is about equimolar. When the reaction is carried out in the presence of water and/or lower alkanol (wherein the lower alkanol has up to 4 carbon atoms), the molar ratio of the imidazole to the aminoglycoside should be about 2:1, as the water/lower alkanol solvents will partially utilize the imidazole reactants.

The ambient temperature utilized in this reaction can be from 5° C. to about 40° C. The reaction is generally a rapid one, from about 0.5-2 hours but can be run over a longer period of time, up to about 24 hours.

When, in my process 1-Z imidazole is utilized wherein Z is lower alkanoyl, the lower alkanoyl protects only the 3''-N-position However, when Z is other than lower alkanoyl, the protecting group will bridge the 3''-N and 4''-O-positions to become a 3''-N, 4''-O-carbonyl moiety. When Gentamicin A, Antibiotic 66-40B, kanamycin A, kanamycin B, 3',4'-dideoxykanamycin B and tobramycin are utilized, a mixture will be obtained wherein bridging will occur not only at the 3''-N and 4''-O-positions, but also at the 3''-N and 2''-O-positions.

The 5-epi-, 5-deoxy-, 5-epi-fluoro-5-deoxy- analogs of this invention are best prepared prior to the introduction of my amino group protection. The preparation of 5-epi-aminoglycosides is described in U.S. Pat. No. 4,000,261. The 5-deoxy aminoglycosides are prepared by procedures similar to those described in copending U.S. Application Ser. No. 701,387, filed June 30, 1976, now U.S. Pat. No. 4,053,591. For instance, a 5-O-thioformyl aminoglycoside (e.g. 5-O-thioformylsisomicin) having all amino functions and all primary and secondary hydroxyl groups protected, is reacted with an organotin hydride (preferably tri-n-butylstannane) in an inert aprotic solvent under an inert atmosphere at temperatures of about 100° C., followed by removal of the protecting groups to obtain the 5-deoxyaminoglycoside (e.g. 5-deoxysisomicin).

The 5-epi-fluoro-5-deoxy aminoglycosides are prepared by procedures similar to those described in copending U.S. Application Ser. No. 792,825, filed May 2, 1977, now abandoned. For instance, an aminoglycoside having a 5-hydroxyl function (e.g. sisomicin) having all its amino and hydroxyl functions protected, other than the 5-hydroxyl function, is reacted with a dialkylaminosulfur trifluoride (e.g. diethylaminosulfur trifluoride) in an inert organic solvent in the temperature range of from −100° C. to about −50° C., followed by removal of the protecting groups to obtain the 5-epi-fluoro-5-deoxyaminoglycoside (e.g. 5-epi-fluoro-5-deoxysisomicin).

The preparation of 1-N-substituted aminoglycosides, for which the compounds of my invention are useful as intermediates, are described in U.S. Pat. No. 4,002,742. I have found, however, that when utilizing a 1-N-unprotected-poly-N-acylaminoglycoside (e.g. 3,2′,6′,3″-tetra-N-acetylsisomicin) for conversion to a 1-N-ethylaminoglycoside (e.g. 1-N-ethylsisomicin), a convenient hydride donor reducing agent to be employed is sodium borohydride.

COMPOSITION-OF-MATTER ASPECT

In its composition-of-matter aspect, this invention relates to novel 1-N-unprotected-poly-N-protected aminoglycosides. Particularly, this invention relates to novel 1-N-unprotected-poly-N-R-3″-N-Z-4,6-di-O-(aminoglycosyl)-1,3-diaminocyclitols, selected from the group consisting of:

3,2′-di-N-R-3″-N-Z-gentamicin A,
3,6′-di-N-R-3″-N-Z-gentamicin B
3,6′,di-N-R-3″-N-Z-gentamicin B$_1$,
3,2′,6′-tri-N-R-3″-N-Z-gentamicin C$_1$,
3,2′,6′-tri-N-R-3″-N-Z-gentamicin C$_{1a}$,
3,2′,6′-tri-N-R-3″-N-Z-gentamicin C$_2$,
3,2′,6′-tri-N-R-3″-N-Z-gentamicin C$_{2a}$,
3,2′,6′-tri-N-R-3″-N-Z-gentamicin C$_{2b}$,
3,2′-di-N-R-3″-N-Z-gentamicin X$_2$,
3,2′,6′-tri-N-R-3″-N-Z-Antibiotic G-52,
3,2′,6′-tri-N-R-3″-N-Z Antibiotic 66-40B,
3,2′,6′-tri-N-R-3″-N-Z Antibiotic 66-40D,
3,2′-di-N-R-3″-N-Z Antibiotic G-418
3,2′,6′-tri-N-R-3″-N-Z Antibiotic JI-20A,
3,2′,6′-tri-N-R-3″-N-Z Antibiotic JI-20B,
3,6′-di-N-R-3″N-Z-kanamycin A,
3,2′,6′-tri-N-R-3″-N-Z-kanamycin B,
3,2′,6′-tri-N-R-3″-N-Z-3′,4′-dideoxykanamycin B,
3,2′,6′-tri-N-R-3″-N-Z-verdamicin,
3,2′,6′-tri-N-R-3″-N-Z-sisomicin,
3,2′,6′-tri-N-R-3″-N-Z-tobramycin, and
the 5-epi, 5-deoxy, 5-epi-fluoro-5-deoxy analogs of the foregoing, wherein R is lower alkanoyl, aroyl, lower alkoxycarbonyl, trichloroethoxycarbonyl, aralkoxycarbonyl, and Z is lower alkanoyl.

The definitions of the protecting groups have been described hereinabove. Specifically, I prefer that both R and Z be lower alkanoyl, preferentially acetyl.

The compounds of this invention are useful in the preparation of 1-N-substituted aminoglycosides. A particularly valuable compound of this invention is 3,2′,6′,3″-tetra-N-acetylsisomicin, which compound is used to obtain 1-N-ethylsisomicin.

The invention described hereinabove is illustrated in detail hereinbelow in the Preparations and Examples, and should not be construed as limiting the scope of my invention.

PREPARATION I

1-N-(2,2,2-Trichloroethoxycarbonyl) imidazole

Dissolve 20 gm. of imidazole in 180 ml. of tetrahydrofuran; cool the resultant solution to 0° C. To this solution, add 31 gm. of 2,2,2-troichloroethylchloroformate in 180 ml. of tetrahydrofuran dropwise over a period of 1 hour. Then stir the mixture at 25° C. for 1 hour, filter the mixture and concentrate the filtrate to dryness. Wash the resultant solid with water and dry to obtain 1-N-(2,2,2-trichloroethoxycarbonyl)imidazole: m.p.=80° C.; ν max. (CHCl$_3$) 3000, 1780, 1400, 1310, 1280, 1235, 1165, 1015 cm.$^{-1}$; δ (CDCl$_3$) 5.03 (2H, s, −CH$_2$CCl$_3$), 7.13 (1H, m, H$_4$), 7.48 (1H, m, H$_5$) and 8.20 ppm (1H, s, H$_2$).

PREPARATION II

N-(2,2,2-Trichloroethoxycarbonyloxy) succinimide

Dissolve 5.75 gm. of N-hydroxysuccinimide in 200 ml. ethyl acetate and 4 gm. of pyridine; cool the resultant solution to 0° C. To this solution, add 10.6 gm. 2,2,2-trichloroethylchloroformate dropwise over a period of 1.5 hours. Filter the resultant mixture and evaporate the filtrate to dryness. Wash the thereby formed needles with hexane to obtain N-(2,2,2-trichloroethoxycarbonyloxy) succinimide, m.p. 98°−101° C.; ν max. (CHCl$_3$) 1825, 1790, 1750, 1185, 826 cm.$^{-1}$, δ (CDCl$_3$) 2.85 (4H, s, −CO(CH$_2$)$_2$ CO−) and 4.90 ppm (2H, s, −COOCH$_2$CCl$_3$).

1-N-unsubstituted-3″-N-unprotected-poly-N-protected-4,6-di-O-(aminoglycosyl)-1,3-diaminocyclitols

PREPARATION III

A. 3,2′,6′-Tri-N-acetylsisomicin

Add cupric acetate hydrate (9 gm., 45 mmol) to a stirred solution of sisomicin (1.3 gm., 2.9 mmol) in water (16 ml.) and dimethylformamide (54 ml.). Stir at room temperature for 35 minutes, then to the cupric salt complex thereby formed, add dropwise at a rate of about 25 drops per minute, 9.3 ml. of a 1 molar solution of acetic anhydride in dimethylformamide (9.3 mmol). Stir the reaction mixture for an additional 30 minutes, then add 30 ml. of water and bubble hydrogen sulfide through the solution for about 10 minutes, stir the mixture for an additional 30 minutes, then filter the solution through a pad of Celite and wash the cupric sulfide residue with three 20 ml. portions of water. Concentrate the combined filtrate and water washings and chromatograph the resultant residue on silica gel (150 gm., 60–200 mesh) eluting with chloroform-methanol-ammonium hydroxide (30:10:1). Combine like fractions as determined by thin layer chromatography and evaporate the fractions containing the major product in vacuo and lyophilize the resultant aqueous mixture to a residue comprising 3,2′,6′-tri-N-acetylsisomicin (1.29 g., 76% yield); [α]$_D^{26}$+186.7° (H$_2$O); δ (D$_2$O) 1.22 (3H, s, 4″-CH$_3$), 1.94, 1.98, 2.00 (9H, s, N-Ac), 2.51 (3H, s, 3″-N-CH$_3$), 2.59 (1H, d, J$_2$″, $_3$″ 9.5 Hz, H$_3$″), 5.10 (1H, d, J$_1$″, 2′ 4.0 Hz, H$_1$″) and 5.51 ppm (1H, d, J$_1$′, 2′ 2.5 Hz, H$_1$′); m/e 573 [M+], 443, 425, 415, 397, 392, 374, 364, 346, 233, 215, 211, 205, 187, 160.

B. 3,6′-Di-N-acetylkanamycin A

Dissolve 300 mg. of kanamycin A and 1.9 gm. of cupric acetate hydrate in 13.5 ml. of dimethylformamide and 4 ml. of water and stir the mixture at 25° C. for 30 minutes. Then add 0.17 gm. of acetic anhydride in 2 ml. of dimethylformamide and stir for 1 hour at 25° C. Bubble hydrogen sulfide through the solution, filter off the solids and wash with dimethylformamide. Evaporate the filtrate to dryness and chromatograph the residue on a silica gel column (110×2.5 cm) using a chloroform:methanol:3.5% ammonium hydroxide (1:2:1) as the eluant to obtain 3,6'-di-N-acetylkanamycin A (130 mg., 37% yield); $[\alpha]_D^{26}+94.6'$ (H$_2$O); $[\theta]_{290}+1002$ (TaCu); δ (D$_2$O) 2.05 (3H, s, NAc), 2.08 (3H, s, NAc), 5.13 (1H, m, H$_1''$) and 5.41 ppm (1H, m, H$_1'$).

C.
1-N-unsubstituted-3''-N-unprotected-poly-N-acetyl-4,6-di-O-(aminoglycosyl)-1,3-diaminocyclitols In a manner similar to that described in Preparation III A., by utilizing as starting compounds:
gentamicin A,
gentamicin B,
gentamicin B$_1$,
gentamicin C$_1$,
gentamicin C$_{1a}$,
gentamicin C$_2$,
gentamicin C$_{2a}$,
gentamicin C$_{2b}$,
gentamicin X$_2$,
Antibiotic G-52,
Antibiotic 66-40B,
Antibiotiic 66-40D,
Antibiotic G-418,
Antibiotic JI-20A,
Antibiotic JI-20B,
kanamycin B,
3',4'-dideoxykanamycin B,
verdamicin,
tobramycin, and the 5-epi, 5-deoxy, 5-epi-fluoro-5-deoxy analogs of the foregoing and of sisomicin and kanamycin, there is obtained, respectively:
(a) 3,2'-di-N-acetylgentamicin A,
(b) 3,6'-di-N-acetylgentamicin B,
(c) 3,6'-di-N-acetylgentamicin B$_1$,
(d) 3,2',6'-tri-N-acetylgentamicin C$_1$,
(e) 3,2',6'-tri-N-acetylgentamicin C$_{1a}$,
(f) 3,2',6'-tri-N-acetylgentamicin C$_2$,
(g) 3,2',6'-tri-N-acetylgentamicin C$_{2a}$,
(h) 3,2',6'-tri-N-acetylgentamicin C$_{2b}$,
(i) 3,2'-di-N-acetylgentamicin X$_2$,
(j) 3,2',6'-tri-N-acetyl Antiibiotic G-52,
(k) 3,2',6'-tri-N-acetyl Antibiotic 66-40B,
(l) 3,2',6'-tri-N-acetyl Antibiotic 66-40D,
(m) 3,2'-di-N-acetyl Antibiotic G-418,
(n) 3,2',6'-tri-N-acetyl Antibiotic JI-20A,
(o) 3,2',6'-tri-N-acetyl Antibiotic JI-20B,
(p) 3,2',6'-tri-N-acetylkanamycin B,
(q) 3,2',6'-tri-N-acetyl-3',4'-dideoxykanamycin B,
(r) 3,2',6'-tri-N-acetylverdamicin,
(s) 3,2',6'-tri-N-acetyltobramycin, and
(t) the 5-epi, 5-deoxy, 5-epi-fluoro-5-deoxy analogs of the foregoing and of 3,2',6'-tri-N-acetylsisomicin and 3,6'-di-N-acetylkanamycin A.

PREPARATION IV
A. 3,2',6'-Tri-N-(2,2,2-trichloroethoxycarbonyl) gentamicin C$_{1a}$ Add cupric acetate hydrate (2.8 gm., 18 mmol) to a stirred solution of gentamicin C$_{1a}$ (1.0 gm., 2 mmol) in dimethylsulfoxide (56 ml.) at 25° C. Continue stiirring for 1 hour, then to the cupric salt complex thereby formed, add portionwise, N-(2,2,2-trichloroethoxycarbonyloxy) succinimide (1.8 gm., 62 mmol) over a 15 minute period. Continue stirring for 2 hours, then dilute the reaction mixture with 2 N ammonium hydroxide (800 ml.) and extract with ethyl acetate (3×75 ml.).

Evaporate the combined extracts in vacuo and chromatograph the resultant residue on a silica gel column (110×2.5 cm.) eluting first with chloroform (250 ml.) and then eluting with chloroform:methanol:concentrated ammonium hydroxide (7:2:0.1 by volume). Combine the like fractions containing the desired product as determined by thin layer chromatography and evaporate the combined fractions to a residue to 3,2',6'-tri-N-(2,2,2-trichloroethoxycarbonyl) gentamicin C$_{1a}$, (1.51 g., 78% yield);

$[\alpha]_D^{26}+80.0°$ (CHCl$_3$), Γ max. (KBr) 3330, 1730, 1520, 1040, 1025 cm$^{-1}$; δ (CDCl$_3$) 1.14 (3H, broad s, 4''-CH$_3$), 2.55 (3H, broad s, 3''-NCH$_3$) and 4.64 ppm (6H, broad s, NHCOOC$\underline{H}_a$CCl$_3$).

B.
1-N-Unsubstituted-3''-N-unprotected-poly-N-(2,2,2-trichloroethoxycarbonyl)-4,6-di-O-(aminoglycosyl)-1,3-diaminocyclitols In a manner similar to Preparation IV A, by utilizing the starting compounds of Preparation III B inclusive of sisomicin and kanamycin, there are obtained as described in Preparation III B, the analogously 2,2,2-trichloroethoxycarbonyl protected derivatives.

EXAMPLE 1
1-N-Unsubstituted-poly-N-protected-4,6-di-O-(aminoglycosyl)-1,3-diaminocyclitols A. 3,2',6',3''-tetra-N-acetylsisomicin To a solution of 3 g. (5.2 mmol) 3,2',6'-tri-N-acetylsisomicin in 150 ml. of water, add 572 mg. (5.2 mmol) of 1-acetylimidazole in 8 ml. of tetrahydrofuran. Stir the solution at room temperature for 30 minutes and then add 572 mg (5.2 mmol) of acetylimidazole. Stir the solution a further 2 hours and then evaporate off the solvent and chromatograph the residue on 150 g. of silica gel, eluting with the lower phase of a chloroform-methanol-15% ammonium hydroxide (2:1:1) solvent mixture to obtain 3,2',6',3''-tetra-N-acetylsisomicin (1.96 g., 61% yield) $[\alpha]_D^{26}+204°$ (H$_2$O); (D$_2$O) 1.05 (rotamers, C-C$\underline{H}_3$), 2.25, 2.05, 1.95 (12H, COC$\underline{H}_3$), 3.1, 3.0, (3H, rotamers, N-C$\underline{H}_3$), 4.85 (1H, m, H-4'), 5.3 (1H, m, H—$_1'$, J=4 Hz) and 5.5 ppm (1H, d, J=2 Hz, H—$_1'$).

B. 3,6',3''-Tri-N-acetylkanamycin A

To a solution of 100 mg. of 3,6'-di-N-acetylkanamycin A in 10 ml. of (1:1) tetrahydrofuran:water, add 29.1 mg. of acetylimidazole and stir the mixture at 25° C. for 23 hours. Evaporate the solution to dryness and chromatograph the residue on a silica gel column (110×1.5 cm) using chloroform:methanol:3.5% ammonium hydroxide (1:2:1) as the eluant to obtain 3,6',3''-tri-N-acetylkanamycin A (41 mg., 38% yield); $[\alpha]_D^{26}+104.7°$ (H$_2$O); δ (D$_2$O) 2.02 (3H, s, NAc), 2.07 (3H, s, NAc), 2.09 (3H, s, NAc), 5.17 (1H, d, J$_1''$, 2'', 3.5 Hz, H$_1''$), and 5.41 ppm (1H, d, J$_1'$, 2' 3.0 Hz, H$_1'$).

C.
1-N-unsubstituted-poly-N-acetyl-4,6-di-O-(aminoglycosyl)-1,3-diaminocyclitols In a manner similar to Example 1A, by utilizing as starting compounds, the products of Preparation III B and III C, there are obtained respectively:
(a) 3,2',3''-tri-N-acetylgentamicin A,
(b) 3,6',3''-tri-N-acetylgentamicin B,
(c) 3,6',3''-tri-N-acetylgentamicin B$_1$, (d) 3,2',6',3''-tetra-N-acetylgentamicin C$_1$,
(e) 3,2',6',3''-tetra-N-acetylgentamicin C$_{1a}$,
(f) 3,2',6',3''-tetra-N-acetylgentamicin C$_2$,
(g) 3,2',6',3''-tetra-N-acetylgentamicin C$_{2a}$,
(h) 3,2',6',3''-tetra-N-acetylgentamicin C$_{2b}$,
(i) 3,2',3''-tri-N-acetylgentamicin X$_2$,
(j) 3,2',6',3''-tetra-N-acetyl Antibiotic G-52,
(k) 3,2',6',3''-tetra-N-acetyl Antibiotic 66-40B,
(l) 3,2',6',3''-tetra-N-acetyl Antibiotic 66-40D,
(m) 3,2',3''-tri-N-acetyl Antibiotic G-418,
(n) 3,2',6',3''-tetra-N-acetyl Antibiotic JI-20A,
(o) 3,2',6',3''-tetra-N-acetyl Antibiotic JI-20B,
(p) 3,2',6',3''-tetra-N-acetylkanamycin B,
(q) 3,2',6',3''-tetra-N-acetyl-3',4'-dideoxykanamycin B,
(r) 3,2',6',3''-tetra-N-acetylverdamicin,
(s) 3,2',6',3''-tetra-N-acetyltobramycin, and the 5-epi, 5-deoxy, 5-epi-fluoro-5-deoxy analogs of the foregoing and of 3,2',6',3''-tetra-N-acetylsisomicin, and of 3,6',3''-tri-N-acetylkanamycin A.

D.
3,2',6'-Tri-N-(2,2,2-trichloroethoxycarbonyl)-3''-N-acetylgentamicin C$_{1a}$ Dissolve 500 mg. of 3,2',6'-tri-N-(2,2,2-trichloroethoxycarbonyl)-gentamicin C$_{1a}$ in 20 ml. (1:1) tetrahydrofuran and water. Add 84.6 mg. of acetyl imidazole dissolved in 4 ml. tetrahydrofuran. Stir the solution at room temperature for 2 hours. Evaporate the tetrahydrofuran and decant off the remaining water. Dissolve the resultant residue in a small amount of chloroform and wash with water. Evaporate the chloroform and azeotrope the resultant residue with benzene. Chromatograph the azeotroped resultant residue on a silica gel column (30×3 cm) eluting with 10% methanol/chloroform. Combine the fractions to obtain 3,2',6'-tri-N-(2,2,2-trichloroethoxycarbonyl)-3''-N-acetyl gentamicin C$_{1a}$ (428 mg., 82% yield); $[\alpha]_D^{26}$ +69.9° C. (CHCl$_3$); $\nu$ max. (KBr) 1720, 1620 cm.$^{-1}$; $\delta$ (CDCl$_3$) 1.08 (3H, s, 4''—CH$_3$), 2.16 (3H, s, NAc), 3.12 (3H, s, 3''—N—CH$_3$) and 4.76 ppm (6H, s, CO$_2$CH$_2$CCl$_3$).

E.
1-N-Unsubstituted-poly-N-(2,2,2-trichloroethoxycarbonyl)-3''-N-acetyl-4,6-di-O-(aminoglycosyl)-1,3-diaminocyclitols In a manner similar to Example 1C, by utilizing the compounds of Preparation IV B there are obtained the analogous 1-N-unsubstituted-poly-N-(2,2,2-trichloroethoxycarbonyl)-3''-N-acetyl-4,6-di-O-(aminoglycosyl)-1,3-diaminocyclitols.

F. 3,2',6'-Tri-N-(2,2,2-trichloroethoxycarbonyl)-3''-N,4''-O-carbonylgentamicin C$_{1a}$ To a solution of 500 mg. of 3,2',6'-tri-N-(2,2,2-trichloroethoxycarbonyl) gentamicin C$_{1a}$ in 10 ml. of anhydrous tetrahydrofuran, add 624 mg. of 1-N-(2,2,2-trichloroethoxycarbonyl) imidazole and then allow the solution to remain at 25° C. for 24 hours. Evaporate the solution, dissolve the residue in ethyl acetate and wash with water, then dry the ethyl acetate layer over MgSO$_4$. Filter the ethyl acetate layer, evaporate to dryness and chromatograph the residue on a silica gel column (110×2.5 cm) using 4% methanol in chloroform as the eluant to obtain 3,2',6'-tri-N-(2,2,2-trichloroethoxycarbonyl)-3''-N-4''-O-carbonylgentamicin C$_{1a}$ (290 mg., 56% yield [$\alpha]_D^{26}$+78.7° (CHCl$_3$), $\nu$ max. (KBr) 3375, 2940, 1730, 1520 cm.$^{-1}$; $\delta$ (CDCl$_3$) 1.38 (3H, s, 4''-CH$_3$), 2.98 (3H, s, 3''-NCH$_3$), 4.77 (6H, broad s, —CH$_2$CCl$_3$), 5.08 (1H, m, H$_1''$), and 5.43 ppm (1H, m, H$_1'$).

G.
1-N-unsubstituted-3''-N-4''-O-carbonyl-poly-N-(2,2,2-trichloroethoxycarbonyl)-4,6-di-O-(aminoglycosyl)-1,3-diaminocyclitols In a manner similar to Example 1F, by utilizing some of the products of Preparation IV B there are obtained the following compounds, respectively:

(a) 3,6'-di-N-(2,2,2-trichloroethoxycarbonyl)-3''-N-4''-O-carbonylgentamicin B,
(b) 3,6'-di-N-(2,2,2-trichloroethoxycarbonyl)-3''-N-4''-O-carbonylgentamicin B$_1$,
(c) 3,2',6'-tri-N-(2,2,2-trichloroethoxycarbonyl)-3''-4''-O-carbonylgentamicin C$_1$,
(d) 3,2',6'-tri-N-(2,2,2-trichloroethoxycarbonyl)-3''-N-4''-O-carbonylgentamicin C$_2$,
(e) 3,2'6'-tri-N-(2,2,2-trichloroethoxycarbonyl)-3''-N-4''-O-carbonylgentamicin C$_{2a}$,
(f) 3,2',6'-tri-N-(2,2,2-trichloroethoxycarbonyl)-3''-N-4''-O-carbonylgentamicin C$_{2b}$,
(g) 3,2'-di-N-(2,2,2-trichloroethoxycarbonyl)-3''-N-4''-O-carbonylgentamicin X$_2$,
(h) 3,2',6'-tri-N-(2,2,2-trichloroethoxycarbonyl)-3''-N-4'''-O-carbonyl Antibiotic G-52,
(i) 3,2',6'-tri-N-(2,2,2-trichloroethoxycarbonyl)-3''-N-4'''-O-carbonyl Antibiotic 66-40D,
(j) 3,2'-di-N-(2,2,2-trichloroethoxycarbonyl)-3''-N-4''-O-carbonyl Antibiotic G-418,
(k) 3,2',6'-tri-N-(2,2,2-trichloroethoxycarbonyl)-3''-N-4'''-O-carbonyl Antibiotic JI-20A,
(l) 3,2',6'-tri-N-(2,2,2-trichloroethoxycarbonyl)-3''-N-4'''-O-carbonyl Antibiotic JI-20B,
(m) 3,2',6'-tri-N-(2,2,2-trichloroethoxycarbonyl)-3''-N-4''-O-carbonylsisomicin,
(n) 3,2',6'-tri-N-(2,2,2-trichloroethoxycarbonyl)-3''-N-4''-O-carbonylverdamicin, and the 5-epi, 5-deoxy, 5-epi-fluoro-5-deoxy analogs of the foregoing and of 3,2',6'-tri-N-(2,2,2-trichloroethoxycarbonyl)-3''-N,4''-O-carbonylgentamicin C$_{1a}$.

EXAMPLE 2

1-N-Substituted-4,6-di-O-(aminoglycosyl)-1,3-diaminocyclitols

A. 1-N-Ethylsisomicin

To a stirred solution of 40.5 g. of 3,2',6',3''-tetra-N-acetylsisomicin in 500 ml. of isopropanol, add 6.5 ml. of acetaldehyde and 2.3 g. of sodium borohydride in 100 ml. of siopropanol, continue stirring for 3 hours at room temperature. After 3 hours, add water and then remove the isopropanol by evaporation. Add 150 ml. of 50% sodium hydroxide to the residue and heat at 100° C. for 18 hours in an argon atmosphere. Cool the solution, adjust the pH to 6 and treat the solution with 2.15 liter of IRC–50 (NH$_4^+$) ion-exchange resin, hash the resin with water and elute with 2 N aqueous ammonium hydroxide. Concentrate the ammoniacal eluant to dryness and dissolve the residue in the lower phase of a chloroform:isopropanol:14% ammonium hydroxide (2:1:1) solvent mixture and chromatograph on a 300 g. silica gel column utilizing the same solvent to obtain 1-N-ethylsisomicin (25 gm., 80% yield).

B.
1-N-Ethyl-4,6-di-O-(aminoglycosyl)-1,3-diaminocyclitols

1. In a manner similar to Example 2A, by utilizing the products of Example 1A, B and C there are obtained the corresponding 1-N-ethyl-4,6-di-O-(aminoglycosyl)-1,3-diaminocyclitols.
2. In a manner similar to Example 2A, by utilizing the products of Example 1F and G there are obtained the corresponding 1-N-ethyl-4,6-di-O-(aminoglycosyl)-1,3-diaminocyclitols.

EXAMPLE 3

1-N-Acetylsisomicin

To a stirred solution of 3.0 gm. of 3,2',6'-tri-N-(trichloroethoxycarbonyl) sisomicin in 75 ml. of methanol and 15 ml. of water, add 0.55 gm. of N-acetoxysuccinimide. Stir the reactants for 20 hours at room temperature, then add 7 ml. of acetic aciid and 6 gm. of zinc dust and heat the mixture for 2.5 hours. Cool and filter the reaction, washing with methanol. Evaporate the filtrate and dissolve the residue in 30 ml. of water, add a solution of 3 gm. sodium carbonate in 600 ml. of water, and heat to boiling. Filter the formed salts and wash the salts with water..Evaporate the filtrate and reflux the residue with 150 ml. of isopropanol. Filter, evaporate the filtrate and chromatograph the residue on 70 gm. of silica gel, eluting with chloroform, methanol, concentrated ammonia (3:1:0.15). Combine like eluates and evaporate and pass the residue through a column of IRA-401S (OH$^-$) ion-exchange resin, eluting with water. The eluate was lyophilized to give 1-N-acetylsisomicin identical with authentic material. (0.9 gm - 60% yield).

I claim:

1. The process for the selective protection of a 3" amino function in a 1,3"-di-N-unprotected-poly-N-protected-4,6-di-O-aminoglyosyl-1,3-diaminocyclitol, wherein the 6-O-aminoglycosyl has an amino function at the 3" position and hydroxyl functions at the 2" and 4" positions, which comprises the reaction of 1,3"-di-N-unprotected-poly-N-protected-4,6-di-O-aminoglycosyl-1,3-diaminocyclitol in a solvent with no greater than one molar equivalent of available 1-Z imidazole wherein Z is an amino protecting group selected from lower alkanoyl, lower alkoxycarbonyl, benzyloxycarbonyl, trichloroethoxycarbonyl and N-carbonylimidazole.
2. The process of claim 1 when carried out in an inert organic solvent wherein said 1-Z-imidazole is present in about equimolar proportions to said 1,3"-unprotected-poly-N-protected-4,6-di-O-(aminoglycosyl)-1,3-diaminocyclitol.
3. The process of claim 1 when carried out in the presence of water and/or lower alkanol wherein said 1-Z-imidazole is present in about twice molar proportions to said 1,3"-unprotected-poly-N-protected-4,6-di-O-(aminoglycosyl)-1,3-diaminocyclitol.
4. The process of claim 1 wherein said 1-Z-imidazole is 1-lower alkanoylimidazole.
5. The process of claim 4 wherein said 1-lower alkanoylimidazole is 1-acetylimidazole.
6. The process of claim 5 wherein 1-acetylimidazole is reacted in twice molar proportios with 3,2',6'-tri-N-acetylsisomicin in the presence of water and tetrahydrofuran to produce 3,2',6',3"-tetra-N-acetylsisomicin.
7. A 1-N-unprotected-poly-N-R-3"-N-Z-4,6-di-O-(aminoglycosyl)-1,3-diaminocyclitol, selected from the group consisting of:

3,2'-di-N-R-3"-N-Z-gentamicin A,
3,6'-di-N-R-3"-N-Z-gentamicin B,
3,6',-di-N-R-3"-N-Z-gentamicin B$_1$,
3,2',6'-tri-N-R-3"-N-Z-gentamicin C$_1$,
3,2',6'-tri-N-R-3"-N-Z-gentamicin C$_{1a}$,
3,2',6'-tri-N-R-3"-N-Z-gentamicin C$_2$,
3,2',6'-tri-N-R-3"-N-Z-gentamicin C$_{2a}$,
3,2',6'-tri-N-R-3"-N-Z-gentamicin C$_{2b}$,
3,2'-di-N-R-3"-N-Z-gentamicin X$_2$,
3,2',6'-tri-N-R-3"-N-Z Antibiotic G-52,
3,2',6'-tri-N-R-3"-N-Z Antibiotic 66-40B,
3,2',6'-tri-N-R-3"-N-Z Antibiotic 66-40D,
3,2',di-N-R-3"-N-Z Antibiotic G-418,
3,2',6'-tri-N-R-3"-N-Z Antibiotic JI-20A,
3,2',6'-tri-N-R-3"-N-Z Antibiotic JI-20B,
3,6'-di-N-R-3"-N-Z-kanamycin A,
3,2',6'-tri-N-R-3"-N-Z-kanamycin B,
3,2',6'-tri-N-R-3"-N-Z-3',4'-dideoxykanamycin B,
3,2',6'-tri-N-R-3"-N-Z-verdamicin,
3,2',6'-tri-N-R-3"-N-Z-sisomicin,
3,2',6'-tri-N-R-3"-N-Z-tobramycin, and the 5-epi, 5-deoxy, 5-epi-fluoro-5-deoxy analogs of the foregoing wherein R is lower alkanoyl, benzoyl, lower alkoxycarbonyl, trichloroethoxycarbonyl, benzyloxycarbonyl, and Z is lower alkanoyl.

8. A compound of claim 7 wherein R is lower alkanoyl.
9. A compound of claim 8 wherein R and Z are acetyl.
10. A compound of claim 9 which is 3,2',6',3"-tetra-N-acetylsisomicin.

* * * * *